US010947324B2

(12) United States Patent
Nutt et al.

(10) Patent No.: US 10,947,324 B2
(45) Date of Patent: Mar. 16, 2021

(54) FLEXIBLE MANUFACTURING SYSTEM FOR SELECTIVELY PRODUCING DIFFERENT LINEAR ALPHA OLEFINS

(71) Applicant: TPC Group LLC, Houston, TX (US)

(72) Inventors: Michael O. Nutt, Pearland, TX (US); Baiyi Zhao, Pasadena, TX (US)

(73) Assignee: TPC Group LLC, Houston, TX (US)

( * ) Notice: Subject to any disclaimer, the term of this patent is extended or adjusted under 35 U.S.C. 154(b) by 0 days.

(21) Appl. No.: 16/804,265

(22) Filed: Feb. 28, 2020

(65) Prior Publication Data

US 2020/0291140 A1 Sep. 17, 2020

Related U.S. Application Data

(60) Provisional application No. 62/817,638, filed on Mar. 13, 2019.

(51) Int. Cl.
*C08F 2/01* (2006.01)
*C08F 4/642* (2006.01)
(Continued)

(52) U.S. Cl.
CPC ............... *C08F 2/01* (2013.01); *C08F 4/642* (2013.01); *C08F 4/69* (2013.01); *C08F 10/08* (2013.01); *C08F 10/14* (2013.01)

(58) Field of Classification Search
USPC .................................................. 585/513, 523
See application file for complete search history.

(56) References Cited

U.S. PATENT DOCUMENTS 5,859,303 A  1/1999 Lashier
6,828,269 B2 12/2004 Commereuc et al.
(Continued)

FOREIGN PATENT DOCUMENTS

WO  2018170054 A1  9/2018

OTHER PUBLICATIONS

International Search Report and Written Opinion in corresponding application PCT/US2020/020405, dated Jun. 25, 2020.
(Continued)

*Primary Examiner* — Fred M Teskin
(74) *Attorney, Agent, or Firm* — Michael Ferrell

(57) ABSTRACT

A flexible manufacturing system for selectively producing different alpha-olefins from ethylene includes: (a) a reaction section 18 with ethylene feed operative to oligomerize ethylene; (b) a catalyst feed system 12, 14, 16 comprising a plurality of independent homogeneous catalyst feeders connected with the reaction section for alternatively providing different selective homogeneous catalyst compositions to the reaction section; (c) an ethylene recycle column 22 coupled to the reaction section and adapted to receive crude product and unreacted ethylene therefrom, the recycle column being operative to separate ethylene and optionally lower oligomers from the crude product which are recycled to the ethylene feed to the reaction section, the ethylene recycle column being further operative to provide a crude product bottoms stream; (d) a catalyst removal section 20 coupled to the reaction section adapted to remove spent catalyst from the system; and (e) a first product separation column 24 connected to the recycle column receiving the crude product stream therefrom, the product separation column being operative to separate purified oligomer from the crude product stream. Optionally provided is a second product separation column 26.

20 Claims, 1 Drawing Sheet

(51) Int. Cl.
*C08F 10/14* (2006.01)
*C08F 10/08* (2006.01)
*C08F 4/69* (2006.01)
*C07C 2/30* (2006.01)
*C07C 2/36* (2006.01)
*C07C 11/02* (2006.01)
*C07C 11/08* (2006.01)
*C07C 11/107* (2006.01)

(56) References Cited

U.S. PATENT DOCUMENTS

| | | |
|---|---|---|
| 7,297,832 B2 | 11/2007 | Blann et al. |
| 7,511,183 B2 | 3/2009 | Blann et al. |
| 8,076,523 B2 | 12/2011 | Bollman et al. |
| 8,076,524 B2 | 12/2011 | Lattner et al. |
| 9,029,619 B2 | 5/2015 | Vermeiren |
| 9,487,456 B2 | 11/2016 | Overett et al. |
| 9,499,456 B2 | 11/2016 | Overett et al. |
| 9,533,923 B2 | 1/2017 | Mogorosi et al. |
| 9,896,392 B2 * | 2/2018 | Meiswinkel ............ B01J 31/143 |
| 9,931,622 B2 | 4/2018 | Magna et al. |
| 10,022,698 B2 | 7/2018 | Shaik et al. |
| 10,059,786 B2 | 8/2018 | Kim et al. |
| 2009/0270567 A1 | 10/2009 | Small et al. |
| 2012/0029258 A1 * | 2/2012 | Wohl .................... B01J 31/189 585/527 |
| 2013/0102826 A1 | 4/2013 | Lattner et al. |
| 2013/0303817 A1 | 11/2013 | Shaik et al. |
| 2016/0207849 A1 | 7/2016 | Stochniol et al. |
| 2017/0158581 A1 | 6/2017 | Bader et al. |
| 2017/0179122 A1 | 6/2017 | Fu et al. |
| 2018/0179122 A1 | 6/2018 | Boutrot et al. |

OTHER PUBLICATIONS

S. Mukherjee et al., "Selective Ethylene Oligomerization with Nickel Oxime Complexes," Organometallics, 2009, 3074-3078, 28, American Chemical Society.

A. Bollmann, et al., "Ethylene Tetramerization: A New Route to Produce 1-Octene in Exceptionally High Selectivities", Journal of the American Chemical Society, 2004, 14712-14713, 126, American Chemical Society.

AlphaButol® The Leading Process for Making High Purity 1-Butene Through Ethylene Dimerization (licensing brochure), 2018, pp. 1-2, Axens.

AlphaHexol™ A New Process for Making High Purity 1-Hexene Through Ethylene Trimerization (licensing brochure), 2018, pp. 1-2, Axens.

G. Ballal, "1-Hexene Production by Axens Alphahexol™ Process", Process Economics Program (PEP) Review Nov. 2012, Sep. 2012, Abstract and pp. i-v, IHS Chemical, Santa Clara, California.

* cited by examiner

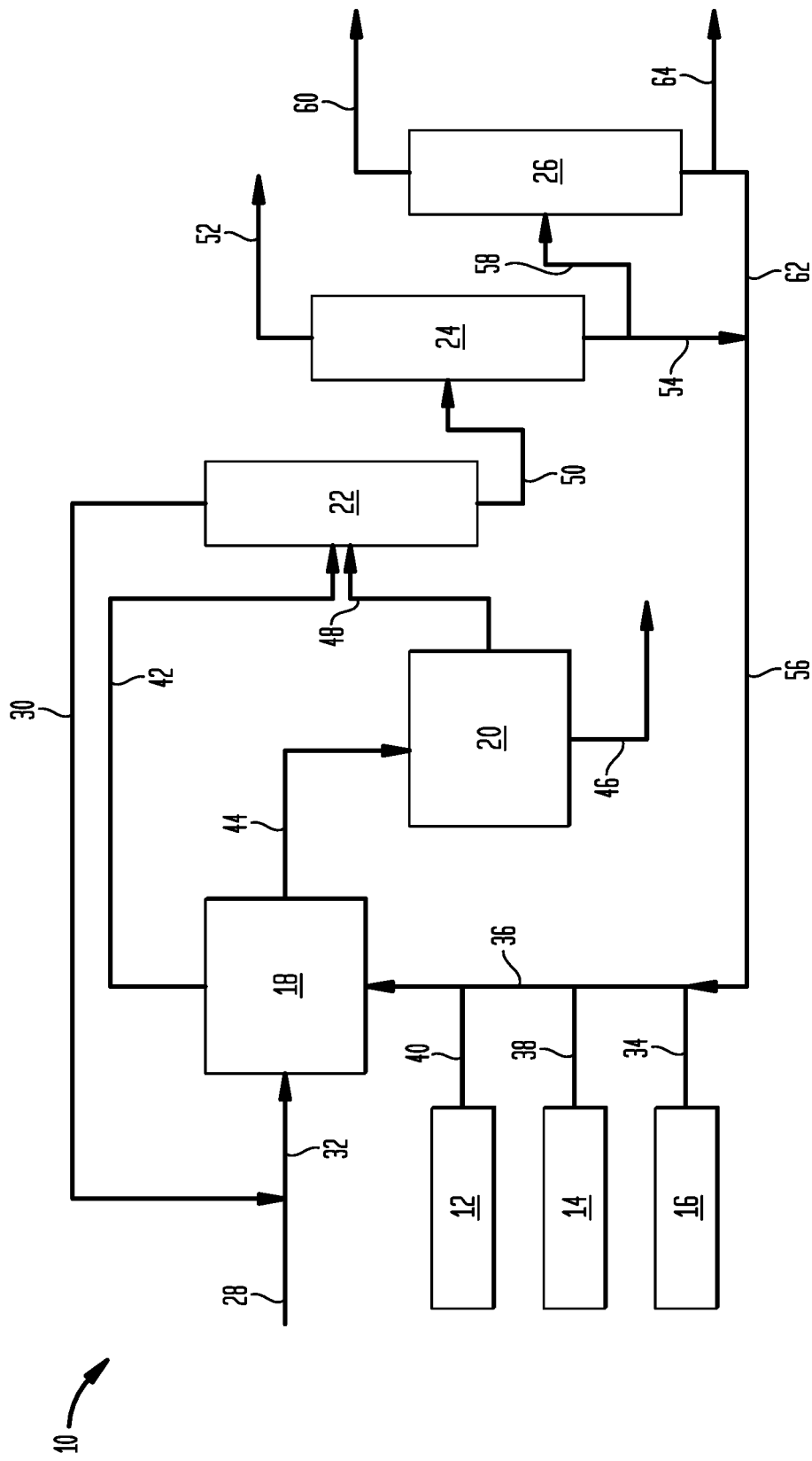

FLEXIBLE MANUFACTURING SYSTEM FOR SELECTIVELY PRODUCING DIFFERENT LINEAR ALPHA OLEFINS

CLAIM FOR PRIORITY

This application is based on U.S. Provisional Patent Application No. 62/817,638 of the same title, filed 13 Mar. 2019, the priority of which is hereby claimed and the disclosure of which is incorporated herein by reference.

TECHNICAL FIELD

The present invention relates to manufacturing linear alpha olefins by ethylene dimerization, trimerization and tetramerization using a flexible oligomerization system which can manufacture different products at different times by using different selective homogeneous catalysts.

BACKGROUND

Flexible manufacturing systems have been proposed in the art for products such as polyisobutylene which can be produced in a single apparatus because of shared product attributes which do not require substantially different reactors or substantially different work-up of the crude product. See U.S. Pat. No. 10,059,786 (Daelim) which discloses an apparatus for polymerizing isobutylene using different catalyst feeds for making different grades of polyisobutylene. $BF_3$ catalyst is used for making highly reactive (HR) PIB or aluminum trichloride catalyst is used for making conventional PIB. See Examples 1, 3, as well as FIG. 1 of U.S. Pat. No. 10,059,786.

Different linear alpha olefin oligomers, on the other hand, require different catalysts for selective production as well as different product purification and are conventionally made in dedicated systems for selectively making one product, or use a reactor provided with non-selective catalysts with multiple separations to isolate a single product from a mixed stream.

U.S. Pat. No. 8,076,524 (ExxonMobil) discloses oligomerizing ethylene with different homogeneous catalysts which are selective for a given product. United States Patent Application Publication No. US 2017/0158581 (Axens) discloses a process for making butene-1 selectively by oligomerizing ethylene; the catalyst used is a mixture of LC2253 Alphabutol® catalyst and triethyl aluminum co-catalyst. The LC2253 catalyst is reportedly a titanium-based homogeneous catalyst. U.S. Pat. No. 9,029,619 (Total Research and Technology) discloses a process for making alpha-olefins from ethanol, which is dehydrated, oligomerized to multiple products and separated into different oligomers by distillation. FIG. 1 of U.S. Pat. No. 9,029,619 is representative. U.S. Pat. No. 10,022,698 (Saudi Arabian Oil Company) discloses a method and apparatus for oligomerizing ethylene, mostly to butene-1. The apparatus includes an internal baffle, single pass reactor. U.S. Pat. No. 9,931,622 (IFP Energies Nouvelles) discloses a process for making butene-1 from ethylene using a titanium/trialkyl aluminum catalyst system. See Table 1, col. 7. Nickel oxime complex catalysts for use in ethylene oligomerization are disclosed in "Selective Ethylene Oligomerization with Nickel Oxime Complexes", (S. Mukherjee et al., Organometallics 2009, 28, 3074-3078, American Chemical Society).

U.S. Pat. No. 9,533,923 (Sasol Technology (Proprietary) Limited) discloses a process for oligomerization of ethylene to mixtures of 1-hexene and 1-octene. U.S. Pat. No. 9,499,456 (Sasol Technology (Proprietary) Limited) discloses a process for co-producing octene-1 and polyethylene from ethylene. U.S. Pat. No. 9,487,456 (Sasol Technology (Proprietary) Limited) discloses a process for tetramerization of ethylene to octene-1 and hexene-1. See Table 1, cols. 21-22. U.S. Pat. No. 8,076,523 (Sasol Technology (PTY) Limited) discloses a process for producing ethylene oligomers in the presence of both a tetramerization catalyst and another catalyst. Typical products include mixtures of 1-octene and 1-hexene. Typical products include mixtures of 1-octene and 1-hexene. U.S. Pat. No. 7,511,183 (Sasol Technology (PTY) Limited) likewise discloses a process for producing 1-octene and hexane from ethylene. U.S. Pat. No. 7,297,832 (Sasol Technology (PTY) Limited) discloses a catalyst and process for oligomerizing ethylene, mostly to octene-1 with high selectivity. U.S. Pat. No. 7,511,183 (Sasol Technology (PTY) Limited) likewise discloses a process for producing 1-octene and hexane from ethylene, while U.S. Pat. No. 7,297,832 (Sasol Technology (PTY) Limited) discloses a catalyst and process for oligomerizing ethylene, mostly to octene-1 with high selectivity. Production of 1-octene from ethylene is also discussed in "Ethylene Tetramerization: A New Route to Produce 1-Octene in Exceptionally High Selectivities" (A. Bollmann, et al., Journal of the American Chemical Society, 2004, 126, 14712-14713, American Chemical Society).

United States Patent Application Publication No. US 2016/0207849 (Evonik Degussa GmbH) discloses a system and method for co-producing butene and octene. The system uses 2 reactors with different heterogeneous catalysts and is based on ethylene feed. The output of the reactors is combined and fed to a series of distillation columns where the products are separated. Different reaction systems are required for the different heterogeneous catalysts.

United States Patent Application Publication No. US 2013/0102826 (Lattner et al., Houston based) discloses an apparatus and method for oligomerizing ethylene to butene using a reactor which vaporizes product along with solvent, while catalyst and activators remain in liquid phase.

United States Patent Application Publication No. US 2009/0270567 (Chevron Phillips) discloses a system and process for oligomerizing ethylene in continuous reactors. The product mix depends upon the catalyst employed. See the text at page 5, second column, as well as FIG. 2.

It will be appreciated from the foregoing references that existing manufacturing systems for alpha olefin oligomers are dedicated either to a single product or to a broad range of mixed products requiring multiple and expensive separations in terms of both operating and capital costs. Moreover, the market for C10+ products is more variable than C4, C6 or C8 products, making production of a wide range of oligomers undesirable in many cases.

Systems dedicated to a single product involve high capital costs for each product. For example, current capital costs for a 30,000 tpy 1-butene AlphaButol® installation are estimated to be 18 million dollars, see AlphaButol® THE LEADING PROCESS FOR MAKING HIGH PURITY 1-BUTENE THROUGH ETHYLENE DIMERIZATION (licensing brochure, Axens, 2018), while costs for a 1-hexene installation for 40,000 tpy are estimated to be more than twice as much at 37 million dollars, see AlphaHexol™ A NEW PROCESS FOR MAKING HIGH PURITY 1-HEXENE THROUGH ETHYLENE TRIMERIZATION (licensing brochure Axens 2018). Production of 1-hexene was also discussed in "1-HEXENE PRODUCTION BY AXENS ALPHAHEXOL™ PROCESS" (G. Ballal, September 2012, Process Economics Program (PEP) Review 2012-11, Santa Clara, Calif.); see Abstract.

The present invention provides for a flexible manufacturing system which can selectively produce 1-butene or 1-hexene and optionally 1-octene and 1-hexene at a fraction of the capital cost for multiple dedicated systems and without the capital and operating costs of providing separation of multiple products from a wide distribution of products from the reaction system.

SUMMARY OF INVENTION

A flexible manufacturing system for selectively producing different alpha-olefins from ethylene includes: a reaction section with ethylene feed operative to oligomerize ethylene; a catalyst feed system comprising a plurality of independent homogeneous catalyst feeders connected with the reaction section for alternatively providing different selective homogeneous catalyst compositions to the reaction section; an ethylene recycle column coupled to the reaction section and adapted to receive crude product and unreacted ethylene therefrom, the recycle column operates to separate ethylene and optionally lower oligomers from the crude product which are recycled to the ethylene feed to the reaction section; the ethylene recycle column being further operative to provide a crude product bottoms stream. A catalyst removal section coupled to the reaction section removes spent catalyst from the system; and a first product separation column connected to the recycle column receives the crude product stream therefrom. The product separation column separates purified oligomer from the crude product stream. A second product separation column is optional, but preferred when making 1-octene.

The system is especially useful for sequentially producing different alpha-olefins from ethylene in the same manufacturing system, without the need for a manufacturing system dedicated to selective production of only one or two oligomers. That is, the flexible manufacturing system may be operated sequentially with different homogeneous catalysts to selectively produce different alpha olefin products.

Further features and advantages will become apparent from the discussion which follows.

BRIEF DESCRIPTION OF DRAWING

The invention is described in detail below with reference to the FIGURE, wherein:

FIG. 1 is a schematic diagram of a system according to the present invention for oligomerizing ethylene selectively into 1-butene, 1-hexene or 1-octene.

DETAILED DESCRIPTION

The invention is described in detail below with reference to FIG. 1. Such discussion is for purposes of illustration only. Modifications within the spirit and scope of the present invention, set forth in the appended claims, will be readily apparent to those of skill in the art. Terminology used throughout the specification and claims herein is given its ordinary meaning. Unless otherwise indicated, percent, % and like terminology refers to weight % (percent). Terminology is further defined below.

"Conversion", "selectivity" and yield are related by the mathematical definition X(conversion)*S(selectivity)=Y (yield), all calculated on a weight basis unless otherwise indicated. For example, if 90% of substance A is converted (consumed), but only 80% of it is converted to the desired substance B and 20% to undesired by-products, so conversion of A is 90%, selectivity for B 80% and yield of substance B is 72% (=90%*80%). Specific values for conversions, selectivities and yields herein refer to the production of alpha olefins from ethylene.

By providing an oligomerization system that has at least two independent homogeneous catalyst feed systems and having the reactors and separation systems designed such that they can accommodate different product slates, versatility with different targeted oligomer products can be obtained by running the system in a first campaign to make a targeted product and then switching catalysts and adjusting purification parameters to make a different targeted product in a second campaign.

Referring to FIG. 1, there is shown a flexible manufacturing system for selectively producing different linear alpha olefins. The system 10 includes a catalyst delivery system with three different independent catalyst feeders, 12, 14, 16, a reactor system RXTR(S) 18 a catalyst removal section, 20, a recycle column 22, a light product separation column 24, and optionally a heavy column 26 for heavier product separation.

The catalyst feeders 12, 14 and 16 contain different homogeneous catalysts and operate independently from each other. Feeder 12 may contain a homogeneous titanate/trialkyl aluminum catalyst for selectively oligomerizing ethylene to butene-1; while feeder 14 may contain a homogeneous chromium/trialkyl aluminum catalyst for selectively oligomerizing ethylene to 1-hexene and feeder 16 may contain a homogeneous catalyst for selectively oligomerizing ethylene to 1-octene with 1-hexene also present in the product.

In operation, fresh ethylene is provided to the system via line 28, mixed with recycle from line 30, and provided to RXTR(S) at 32. Catalyst is provided to RXTR(S) 18 from one of the catalyst feeders 12, 14, or 16 depending on the desired product. That is, homogeneous catalyst can be provided from feeder 16 via lines 34, 36; homogeneous catalyst may be provided from feeder 14 via lines 38, 36; or homogeneous catalyst from feeder 12 via lines 40, 36.

If a mixture of the product is desired, catalyst from more than one of the catalyst feeders may be employed.

Crude product and unreacted ethylene is withdrawn from the RXTR(S) 18 via line 42 and fed to column 22. Crude product, unreacted ethylene and optionally solvent and spent catalyst is withdrawn from RXTR(S) 18 via line 44 and provided to the catalyst removal system 20 where spent catalyst is separated and removed from the product via line 46 and additional crude product is provided to column 22 via line 48.

In column 22, lights, usually predominantly ethylene, are separated from the crude product and recycled back as feed at 32 to RXTR(S) 18 via line 30, while the crude product as partially purified is sent to column 24 via line 50. In column 24, lights, usually a purified product stream is drawn off via line 52 while bottoms are provided via lines 54 and 56 to line 36 as solvent for homogeneous catalyst or provided to column 26 via line 58 for further processing.

While typically mostly ethylene is recycled by column 22, conditions may be altered to recycle oligomers as well, depending on the target product and catalyst. Likewise, oligomers may be co-fed as fresh feed to the system with ethylene, depending upon availability, the target product and catalyst provided to the reaction section.

In column 26, the bottoms from column 24 are separated into an overhead product stream 60 and a bottoms stream which may be recycled as catalyst solvent via line 62 or forwarded for further processing via line 64.

Using at least two catalyst feeders, one first employs a catalyst system that is targeted for the production of 1-butene while a second catalyst for production of hexene-1 is sequestered in a different catalyst feeder. The unit operators can start a campaign making butene-1 to fill orders for a set amount of time (1 week, 1 month, 1 quarter etc.) and switch to the secondary catalyst feed system and adjust system parameters to transition to making hexene-1. A third catalyst delivery system may be present to make on-purpose octene-1 in the next campaign or to keep capital low, the original system could be isolated, cleared, cleaned, and commissioned with the new catalyst. This is one of the major benefits of employing a homogeneous catalyst system where a unit shutdown and catalyst change is not necessary to make new products. To accommodate this flexibility, the reactor and purification systems may have to be customized to the most rigorous/difficult process. This could include the addition of parallel reactors, chillers/heaters, and solvent recycle systems to allow for different residence times and capacities. Below are some of the factors to consider in a system and process design:

To provide the flexible manufacturing system of the invention, one designs to the maximum reactor pressure (600-650 psig) and temperature (140-150° C.) with turn-down capability depending on the target products. Likewise, metallurgy is selected to accommodate all of the titanate, chromium and co-catalysts noted above. Columns 22, 24 and 26 are provided reboilers, condensers, compressors and the like to accommodate the various modes of operation and the required separations.

The purification system is adapted for the most difficult separations but may be operated differently for each target product. In FIG. 1, there is shown a preferred system for the production of butene-1, hexene-1 and octene-1 in a single unit. In the case of a catalyst system that makes a high selectivity product like butene-1, only columns 22 and 24 are needed so stream 58 can be directed a product tank (bypassing Column 26). To make octene-1 or higher oligomers, all three of columns 22, 24, and 26 are used due to

|  | 1-Butene | 1-Hexene | 1-Octene/1-Hexene |
|---|---|---|---|
| Catalyst | Ti(OR)4/Al(Et)3 | Cr/AlR3 | (Cr+3/PNP)/MAO |
| Temperature, ° C. | 50 to 60 | 140 | 40 to 60 |
| Pressure, psig (MPa) | 440 (3.034) | 435 (2.99) | 435 to 650 (2.99 to 4.48) |
| Selectivity | 93% for 1-butene | 85% for C6 olefins 99% of which is 1-hexene. | 75% for 1-octene; The sum of 1-hexene and 1-octene is larger than 95%. |
| Conversion (one pass) | 85% or higher | 33% | TOE is about 500,00 g/g Cr/h |
| Reaction | liquid phase | liquid phase | liquid phase |

In many cases, the catalyst is prepared from a transition metal such as titanium, zirconium, chromium, nickel, tantalum, and tungsten. The various catalysts in the above table are described in the literature. Titanate catalysts with organoaluminum cocatalysts selective to 1-butene are described in U.S. Pat. No. 9,931,622 and Publication No. US20180179122. Chromium catalysts with organoaluminum cocatalysts selective to 1-hexene are described in U.S. Pat. No. 6,828,269; while chromium catalysts with phosphino amine and organoaluminum cocatalysts are described in U.S. Pat. Nos. 9,533,923 and 9,487,456. U.S. Pat. Nos. 9,487,456 and 9,533,923 also disclose organoboron activators.

One or more organic ligand(s), co-catalyst(s) and/or modifier(s) may be used in conjunction with the catalyst. Suitable co-catalysts include, but are not limited to, organoaluminum compounds, inorganic borate salts, organic boron compounds, fluorinated aluminate salts, sodium hexafluoroantimonate, $LiAlH_4$, and a mixture of magnesium and aluminum salts.

For example, 1-hexene production using a chromium-based catalyst, a cocatalyst based on magnesium, and an aluminum salt activator is disclosed by Ballal, supra. Nickel-oxime complexes were used with a cocatalyst (e.g., methylaluminoxane (MAO) or diethyl aluminum chloride) in the production of 1-butene, as discussed by Mukherjee, et al., supra. Bollmann et al., supra, teach 1-octene production with chromium complexes; suitable co-catalysts included modified methylaluminoxane (MMAO-3A), ethylaluminoxane (EAO), and silica-supported MAO in combination with trimethylaluminum (TMA).

the increased distribution of products made. For example, if one is targeting making octene-1 but the catalyst system makes the below distribution:

| Product | Reactor Outlet Wt % | Selectivity Wt % |
|---|---|---|
| Ethylene | 50 | — |
| Butene-1 | 2.5 | 5 |
| Hexene-1 | 10 | 20 |
| Octene-1 | 35 | 70 |
| C10+ | 2.5 | 5 | then the three column configuration in FIG. 1 is preferred where both ethylene and butene-1 are recycled back to the reactor as feeds in line 30, hexene-1 is purified in column 24 and exits via line 52, while octene-1 is purified in column 26 and exits in line 60. An additional tower to purify butene-1 from hexene-1 could be installed if so desired; however, using very selective catalyst systems allow for not requiring additional towers. One could also recycle hexene-1 in column 22 back to the reactor to eliminate the need of column 26 as long as the catalyst system is flexible enough to react hexene-1 with ethylene to make octene-1. In general, a relatively heavy solvent is used to carry the catalyst through to the reactor system. It is typically a target product like butene-1, hexene-1 or octene-1, so the towers will need to be connected to the catalyst feeds so that if tower 26 is out of service, that tower 24 bottoms will be used to recycle back to the catalyst delivery systems.

Adjustments to the purification system operating conditions are likewise needed depending on the targeted product. Below are the various product boiling points at different pressures (English and Metric Units) that would require flexibility in the purification section when making different target molecules using the same reaction and purification systems. As pressure increases, temperature requirements continue to increase and the tower metal thickness required also increases, making designs for excessively high pressures expensive to build and operate. Ideally, the pressure is just high enough in the product separation columns to push the product into the product tanks if so desired and to make sure products like C4s in the overhead condense with cooling water. That said, one may target the product separating column operating pressure to be higher for butene-1 to allow for condensing with cold water, but then run the column at lower pressures when targeting octene-1 so that you don't have to put so much energy in.

| Pressure [PSIA] | Butene-1 [° F.] | Hexene-1 [° F.] | Octene-1 [° F.] |
|---|---|---|---|
| 14.7 | 21 | 145 | 249 |
| 20 | 35 | 163 | 271 |
| 30 | 56 | 190 | 300 |
| 40 | 72 | 209 | 321 |
| 50 | 85 | 224 | 339 |

Note:
15# steam = 216° F.
150# steam = 360° F.

| Pressure [MPa, A] | Butene-1 [° C.] | Hexene-1 [° C.] | Octene-1 [° C.] |
|---|---|---|---|
| 0.101 | −6.1 | 62.8 | 120.5 |
| 0.138 | 1.7 | 72.7 | 132.8 |
| 0.206 | 13.3 | 87.8 | 148.9 |
| 0.276 | 22.2 | 98.3 | 160.5 |
| 0.345 | 29.4 | 106.7 | 170.5 |

Note:
0.13 MPa steam = 102° C.
1.034 MPa steam = 182° C.

As one changes production from a C4 product to a C8 product, the final tower reboiler will need to shift from a low grade heat source like a waste condensate (hot water) or 15# (0.13 MPa) steam to a more typical 150# (1.034 MPa) steam depending on the operating pressure of the tower. If operating the system to make butene-1, one may utilize waste heat from the ethylene recycle tower or other sources and avoid using 150# (1.034 MPa) steam. A dedicated system for making butene-1 using only waste heat or low pressure steam would not be able to purify a C6 or C8 product without modifications to add alternative heat sources. The invention design allows for the flexibility to target/optimize the purification section around the product that is targeted; preferably it covers a range from C4 to C8, and possibly up to C10+ if a suitable selective catalyst system is employed. This is also true for the multiple configurations where there is a third separation or "heavies" tower as, for Example tower 26 in FIG. 1 discussed above, that could be used in connection with catalyst systems which are less selective and make a wider range of oligomers.

Summary of Preferred Embodiments

There is thus provided in accordance with the present invention Embodiment No. 1 which is a flexible manufacturing system for selectively producing different alpha-olefins from ethylene comprising:

(a) a reaction section with ethylene feed operative to oligomerize ethylene;
(b) a catalyst feed system comprising a plurality of independent homogeneous catalyst feeders connected with the reaction section for alternatively providing different selective homogeneous catalyst compositions to the reaction section;
(c) an ethylene recycle column coupled to the reaction section and adapted to receive crude product and unreacted ethylene therefrom, the recycle column being operative to separate ethylene and optionally lower oligomers from the crude product which are recycled to the ethylene feed to the reaction section, the ethylene recycle column being further operative to provide a crude product bottoms stream;
(d) a catalyst removal section coupled to the reaction section adapted to remove spent catalyst from the system; and
(e) a first product separation column connected to the recycle column receiving the crude product stream therefrom, the product separation column being operative to separate purified oligomer from the crude product stream.

Embodiment No. 2 is the flexible manufacturing system for selectively producing different alpha-olefins according to Embodiment No. 1, wherein one of the homogeneous catalyst feeds is provided a first homogeneous catalyst composition comprising a titanate catalyst and an organo aluminum cocatalyst, the first homogeneous catalyst composition being selective for 1-butene.

Embodiment No. 3 is the flexible manufacturing system for selectively producing different alpha-olefins according to Embodiment Nos. 1 or 2, wherein one of the homogeneous catalyst feeders is provided a second homogeneous catalyst composition comprising a chromium catalyst and an organoaluminum cocatalyst, the second homogeneous catalyst composition being selective for 1-hexene.

Embodiment No. 4 is the flexible manufacturing system for selectively producing different alpha-olefins according to Embodiment No. 3, wherein a magnesium compound cocatalyst is also provided to the catalyst feeders.

Embodiment No. 5 is the flexible manufacturing system for selectively producing different alpha-olefins according to any one of Embodiment Nos. 1-4 wherein one of the homogeneous catalyst feeders is provided a third homogeneous catalyst composition comprising a chromium catalyst, a phosphino amine cocatalyst and an organoaluminum cocatalyst, the third homogeneous catalyst composition being selective for 1-octene and 1-hexene.

Embodiment No. 6 is the flexible manufacturing system for selectively producing different alpha-olefins according to any one of Embodiment Nos. 1-5, wherein the first product separation column is connected to provide bottoms to the catalyst feed system as solvent for homogeneous catalyst compositions.

Embodiment No. 7 is the flexible manufacturing system for selectively producing different alpha-olefins according to any one of Embodiment Nos. 1-6, further comprising a second product separation column coupled to the first product separation column to receive bottoms therefrom and separate the bottoms from the first column into an overhead oligomerized product stream and a bottoms stream.

Embodiment No. 8 is the flexible manufacturing system for selectively producing different alpha-olefins according to Embodiment No. 7, wherein the second product separation column is connected to provide bottoms to the catalyst feed system as solvent for homogeneous catalyst compositions.

Embodiment No. 9 is the flexible manufacturing system for selectively producing different alpha-olefins according to any one of Embodiment Nos. 1-8, operated with a homogeneous catalyst composition comprising a titanate catalyst and organoaluminum cocatalyst selective for 1-butene, wherein selectivity to 1-butene is at least 85 weight % based on ethylene consumption.

Embodiment No. 10 is the flexible manufacturing system for selectively producing different alpha-olefins according to any one of Embodiment Nos. 1-9, wherein the homogeneous catalyst composition further comprises a magnesium compound cocatalyst.

Embodiment No. 11 is the flexible manufacturing system for selectively producing different alpha-olefins according to any one of Embodiment Nos. 1-10, operated with a homogeneous catalyst composition comprising a chromium catalyst and an organoaluminum cocatalyst selective for 1-hexene, wherein selectivity to 1-hexene is at least 75 weight % based on ethylene consumption.

Embodiment No. 12 is the flexible manufacturing system for selectively producing different alpha-olefins according to any one of Embodiment Nos. 1-11, further comprising a second product separation column coupled to the first product separation column to receive bottoms therefrom and separate the bottoms from the first column into an overhead oligomeric product stream and a bottom stream and operated with a homogeneous catalyst composition comprising a chromium catalyst, a phosphino amine cocatalyst, and an organoaluminum cocatalyst, the catalyst being selective for 1-octene and 1-hexene, wherein 1-hexene is withdrawn as a product from the overhead of the first product separation column and 1-octene is withdrawn as a product from the second product separation column and wherein selectivity to 1-octene is at least 65 weight % based on ethylene consumption and selectivity to 1-hexene and 1-octene collectively is at least 85 weight % based on ethylene consumption.

Embodiment No. 13 is the flexible manufacturing system for selectively producing different alpha-olefins according to any one of Embodiment Nos. 1-12, wherein at least one of the homogeneous catalyst compositions is a homogeneous transition metal catalyst.

Embodiment No. 14 is the flexible manufacturing system for selectively producing different alpha-olefins according to Embodiment No. 13, wherein the homogeneous transition metal catalyst is prepared from a precursor metal selected from the group consisting of titanium, zirconium, chromium, nickel, tantalum, and tungsten.

Embodiment No. 15 is the flexible manufacturing system for selectively producing different alpha-olefins according to any one of Embodiment Nos. 1-14, wherein one or more of (an) organic ligand(s), (a) co-catalyst(s) and (a) modifier(s) is also provided to the reaction section.

Embodiment No. 16 is the flexible manufacturing system for selectively producing different alpha-olefins according to Embodiment No. 15, wherein the co-catalyst is selected from the group consisting of organoaluminum compounds, inorganic borate salts, organic boron compounds, fluorinated aluminate salts, sodium hexafluoroantimonate, LiAlH$_4$, and a mixture of magnesium and aluminum salts.

Embodiment No. 17 is a method of sequentially producing different alpha-olefins from ethylene in the same manufacturing system comprising:
(a) providing a flexible manufacturing system including a reaction section with ethylene feed operative to oligomerize ethylene;
(ii) a catalyst feed system comprising a plurality of independent homogeneous catalyst feeders connected with the reaction section for alternatively providing different selective homogeneous catalyst compositions to the reaction section;
(iii) an ethylene recycle column coupled to the reaction section and adapted to receive crude product and unreacted ethylene therefrom, the recycle column being operative to separate ethylene and optionally lower oligomers from the crude product which are recycled to the ethylene feed to the reaction section, the ethylene recycle column being further operative to provide a crude product bottoms stream;
(iv) a catalyst removal section coupled to the reaction section adapted to remove spent catalyst from the system;
(v) a first product separation column connected to the recycle column receiving the crude product stream therefrom, the product separation column being operative to separate purified oligomer from the crude product stream; and optionally including
(vi) a second product separation column coupled to the first product separation column to receive bottoms therefrom and separate the bottoms from the first column into an overhead oligomerized product stream and a bottoms stream;
(b) operating the flexible manufacturing system with ethylene feed and a first homogeneous catalyst feed, wherein the first homogeneous catalyst is selective to a first alpha olefin composition;
(c) recovering the first alpha olefin composition; and thereafter
(d) operating the flexible manufacturing system with ethylene feed and a second homogeneous catalyst feed, wherein the second homogenous catalyst feed is selective to a second alpha olefin composition which is different from the first alpha olefin composition; and
(e) recovering the second alpha olefin composition.

Embodiment No. 18 is the method of sequentially producing different alpha-olefins from ethylene in the same manufacturing system according to Embodiment No. 17, wherein the flexible manufacturing system for selectively producing different alpha-olefins is operated in step (b) or step (d) with a homogeneous catalyst composition comprising a titanate catalyst and organoaluminum cocatalyst selective for 1-butene, wherein selectivity to 1-butene is at least 85 weight % based on ethylene consumption.

Embodiment No. 19 is the method of sequentially producing different alpha-olefins from ethylene in the same manufacturing system according to Embodiment No. 17, wherein the flexible manufacturing system for selectively producing different alpha-olefins is operated in step (b) or step (d) with a homogeneous catalyst composition comprising a chromium catalyst and an organoaluminum cocatalyst selective for 1-hexene, wherein selectivity to 1-hexene is at least 75 weight % based on ethylene consumption.

Embodiment No. 20 is the method of sequentially producing different alpha-olefins from ethylene in the same manufacturing system according to Embodiment No. 17, wherein the flexible manufacturing system for selectively producing different alpha-olefins further comprises a second product separation column coupled to the first product separation column to receive bottoms therefrom and separate the bottoms from the first column into an overhead oligomeric product stream and a bottom stream and the system being operated with a homogeneous catalyst composition comprising a chromium catalyst, a phosphino amine cocatalyst, and an organoaluminum cocatalyst, the catalyst being selective for 1-octene and 1-hexene, wherein 1-hexene product is withdrawn as a product from the overhead of the first product separation column and 1-octene is withdrawn as overhead from the second product separation column and wherein selectivity to 1-octene is at least 65 weight % based on ethylene consumption and selectivity to 1-hexene and 1-octene collectively is at least 85 weight % based on ethylene consumption.

Embodiment No. 21 is the method of sequentially producing different alpha-olefins from ethylene in the same manufacturing system according to Embodiment No. 17, comprising sequentially operating the flexible manufacturing system with ethylene feed and three different homogeneous catalysts to selectively produce three different alpha olefin product streams.

Embodiment No. 22 is the method of sequentially producing different alpha-olefins from ethylene in the same manufacturing system according to Embodiment No. 17, wherein at least one of the homogeneous catalyst compositions is a homogeneous transition metal catalyst.

Embodiment No. 23 is the method of sequentially producing different alpha-olefins from ethylene in the same manufacturing system according to Embodiment No. 22, wherein the homogeneous transition metal catalyst is prepared from a precursor metal selected from the group consisting of titanium, zirconium, chromium, nickel, tantalum, and tungsten.

Embodiment No. 24 is the method of sequentially producing different alpha-olefins from ethylene in the same manufacturing system according to Embodiment No. 22, wherein one or more of (an) organic ligand(s), (a) co-catalyst(s) and (a) modifier(s) is also provided to the reaction section.

Embodiment No. 25 is the method of sequentially producing different alpha-olefins from ethylene in the same manufacturing system according to Embodiment No. 24, wherein the co-catalyst is selected from the group consisting of organoaluminum compounds, inorganic borate salts, organic boron compounds, fluorinated aluminate salts, sodium hexafluoroantimonate, $LiAlH_4$, and a mixture of magnesium and aluminum salts.

While the invention has been described in detail, modifications within the spirit and scope of the invention will be readily apparent to those of skill in the art. Such modifications are also to be considered as part of the present invention. In view of the foregoing discussion, relevant knowledge in the art and references discussed above in connection with the Background of the Invention and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of illustration only and is not intended to limit the invention.

We claim:

1. A flexible manufacturing system for selectively producing different alpha-olefins from ethylene comprising:
   (a) a reaction section with ethylene feed operative to oligomerize ethylene;
   (b) a catalyst feed system comprising a plurality of independent homogeneous catalyst feeders connected with the reaction section for alternatively providing different selective homogeneous catalyst compositions to the reaction section;
   (c) an ethylene recycle column coupled to the reaction section and adapted to receive crude product and unreacted ethylene therefrom, the recycle column being operative to separate ethylene and optionally lower oligomers from the crude product which are recycled to the ethylene feed to the reaction section, the ethylene recycle column being further operative to provide a crude product bottoms stream;
   (d) a catalyst removal section coupled to the reaction section adapted to remove spent catalyst from the system; and
   (e) a first product separation column connected to the recycle column receiving the crude product stream therefrom, the product separation column being operative to separate purified oligomer from the crude product stream.

2. The flexible manufacturing system for selectively producing different alpha-olefins according to claim 1, wherein one of the homogeneous catalyst feeds is provided a first homogeneous catalyst composition comprising a titanate catalyst and an organo aluminum cocatalyst, the first homogeneous catalyst composition being selective for 1-butene.

3. The flexible manufacturing system for selectively producing different alpha-olefins according to claim 1, wherein one of the homogeneous catalyst feeders is provided a second homogeneous catalyst composition comprising a chromium catalyst and an organoaluminum cocatalyst, the second homogeneous catalyst composition being selective for 1-hexene.

4. The flexible manufacturing system for selectively producing different alpha-olefins according to claim 3, wherein a magnesium compound cocatalyst is also provided to the catalyst feeders.

5. The flexible manufacturing system for selectively producing different alpha-olefins according to claim 3, wherein one of the homogeneous catalyst feeders is provided a third homogeneous catalyst composition comprising a chromium catalyst, a phosphino amine cocatalyst and an organoaluminum cocatalyst, the third homogeneous catalyst composition being selective for 1-octene and 1-hexene.

6. The flexible manufacturing system for selectively producing different alpha-olefins according to claim 1, wherein the first product separation column is connected to provide bottoms to the catalyst feed system as solvent for homogeneous catalyst compositions.

7. The flexible manufacturing system for selectively producing different alpha-olefins according to claim 1, further comprising a second product separation column coupled to the first product separation column to receive bottoms therefrom and separate the bottoms from the first column into an overhead oligomerized product stream and a bottoms stream.

8. The flexible manufacturing system for selectively producing different alpha-olefins according to claim 7, wherein the second product separation column is connected to provide bottoms to the catalyst feed system as solvent for homogeneous catalyst compositions.

9. The flexible manufacturing system for selectively producing different alpha-olefins according to claim 1, operated with a homogeneous catalyst composition comprising a titanate catalyst and organoaluminum cocatalyst selective for 1-butene, wherein selectivity to 1-butene is at least 85 weight % based on ethylene consumption.

10. The flexible manufacturing system for selectively producing different alpha-olefins according to claim 1, operated with a homogeneous catalyst composition comprising a chromium catalyst and an organoaluminum cocatalyst selective for 1-hexene, wherein selectivity to 1-hexene is at least 75 weight % based on ethylene consumption.

11. The flexible manufacturing system for selectively producing different alpha-olefins according to claim 1, further comprising a second product separation column coupled to the first product separation column to receive bottoms therefrom and separate the bottoms from the first column into an overhead oligomeric product stream and a bottom stream and operated with a homogeneous catalyst composition comprising a chromium catalyst, a phosphino amine cocatalyst, and an organoaluminum cocatalyst, the catalyst being selective for 1-octene and 1-hexene, wherein 1-hexene is withdrawn as a product from the overhead of the first product separation column and 1-octene is withdrawn as a product from the second product separation column and wherein selectivity to 1-octene is at least 65 weight % based on ethylene consumption and selectivity to 1-hexene and 1-octene collectively is at least 85 weight % based on ethylene consumption.

12. The flexible manufacturing system for selectively producing different alpha-olefins according to claim 1, wherein at least one of the homogeneous catalyst compositions is a homogeneous transition metal catalyst.

13. The flexible manufacturing system for selectively producing different alpha-olefins according to claim 12, wherein the homogeneous transition metal catalyst is prepared from a precursor metal selected from the group consisting of titanium, zirconium, chromium, nickel, tantalum, and tungsten.

14. The flexible manufacturing system for selectively producing different alpha-olefins according to claim 1, wherein one or more of (an) organic ligand(s), (a) co-catalyst(s) and (a) modifier(s) is also provided to the reaction section.

15. The flexible manufacturing system for selectively producing different alpha-olefins according to claim 14, wherein the co-catalyst is selected from the group consisting of organoaluminum compounds, inorganic borate salts, organic boron compounds, fluorinated aluminate salts, sodium hexafluoroantimonate, $LiAlH_4$, and a mixture of magnesium and aluminum salts.

16. A method of sequentially producing different alpha-olefins from ethylene in the same manufacturing system comprising:
(a) providing a flexible manufacturing system including a reaction section with ethylene feed operative to oligomerize ethylene;
(ii) a catalyst feed system comprising a plurality of independent homogeneous catalyst feeders connected with the reaction section for alternatively providing different selective homogeneous catalyst compositions to the reaction section;
(iii) an ethylene recycle column coupled to the reaction section and adapted to receive crude product and unreacted ethylene therefrom, the recycle column being operative to separate ethylene and optionally lower oligomers from the crude product which are recycled to the ethylene feed to the reaction section, the ethylene recycle column being further operative to provide a crude product bottoms stream;
(iv) a catalyst removal section coupled to the reaction section adapted to remove spent catalyst from the system;
(v) a first product separation column connected to the recycle column receiving the crude product stream therefrom, the product separation column being operative to separate purified oligomer from the crude product stream; and optionally including
(vi) a second product separation column coupled to the first product separation column to receive bottoms therefrom and separate the bottoms from the first column into an overhead oligomerized product stream and a bottoms stream;
(b) operating the flexible manufacturing system with ethylene feed and a first homogeneous catalyst feed, wherein the first homogeneous catalyst is selective to a first alpha olefin composition;
(c) recovering the first alpha olefin composition; and thereafter
(d) operating the flexible manufacturing system with ethylene feed and a second homogeneous catalyst feed, wherein the second homogenous catalyst feed is selective to a second alpha olefin composition which is different from the first alpha olefin composition; and
(e) recovering the second alpha olefin composition.

17. The method of sequentially producing different alpha-olefins from ethylene in the same manufacturing system according to claim 16, wherein the flexible manufacturing system for selectively producing different alpha-olefins is operated in step (b) or step (d) with a homogeneous catalyst composition comprising a titanate catalyst and organoaluminum cocatalyst selective for 1-butene, wherein selectivity to 1-butene is at least 85 weight % based on ethylene consumption.

18. The method of sequentially producing different alpha-olefins from ethylene in the same manufacturing system according to claim 16, wherein the flexible manufacturing system for selectively producing different alpha-olefins is operated in step (b) or step (d) with a homogeneous catalyst composition comprising a chromium catalyst and an organoaluminum cocatalyst selective for 1-hexene, wherein selectivity to 1-hexene is at least 75 weight % based on ethylene consumption.

19. The method of sequentially producing different alpha-olefins from ethylene in the same manufacturing system according to claim 16, wherein the flexible manufacturing system for selectively producing different alpha-olefins further comprises a second product separation column coupled to the first product separation column to receive bottoms therefrom and separate the bottoms from the first column into an overhead oligomeric product stream and a bottom stream and the system being operated with a homogeneous catalyst composition comprising a chromium catalyst, a phosphino amine cocatalyst, and an organoaluminum cocatalyst, the catalyst being selective for 1-octene and 1-hexene, wherein 1-hexene product is withdrawn as a product from the overhead of the first product separation column and 1-octene is withdrawn as overhead from the second product separation column and wherein selectivity to 1-octene is at least 65 weight % based on ethylene consumption and selectivity to 1-hexene and 1-octene collectively is at least 85 weight % based on ethylene consumption.

20. The method of sequentially producing different alpha-olefins from ethylene in the same manufacturing system according to claim 16, comprising sequentially operating the flexible manufacturing system with ethylene feed and three different homogeneous catalysts to selectively produce three different alpha olefin product streams.

* * * * *